United States Patent [19]
Marble

[11] Patent Number: 5,718,669
[45] Date of Patent: Feb. 17, 1998

[54] INTEGRATED SYNERGISTIC EMERGENCY SPLINT

[75] Inventor: Alan F. Marble, Billings, Mont.

[73] Assignee: Lots Corporation, Kalispell, Mont.

[21] Appl. No.: 399,210

[22] Filed: Mar. 6, 1995

Related U.S. Application Data

[63] Continuation of Ser. No. 54,639, Apr. 27, 1993, abandoned, which is a continuation of Ser. No. 876,736, Apr. 27, 1992, abandoned.

[51] Int. Cl.$^6$ .................................................. A61F 5/05
[52] U.S. Cl. ........................... 602/5; 602/13; 602/20; 602/23; 128/869; 128/DIG. 20
[58] Field of Search ..................... 128/DIG. 20, 869; 602/13, 20, 5, 23

[56] References Cited

U.S. PATENT DOCUMENTS

| | | | |
|---|---|---|---|
| 2,651,302 | 9/1953 | Berry | 602/13 |
| 3,477,428 | 11/1969 | Hare | 602/23 |
| 3,643,656 | 2/1972 | Young et al. | 602/13 |
| 3,745,998 | 7/1973 | Rose | 602/13 X |
| 3,762,404 | 10/1973 | Sakita | 128/DIG. 20 X |
| 3,786,805 | 1/1974 | Tourin | 128/DIG. 20 |
| 3,875,935 | 4/1975 | Drew | 602/5 |
| 3,978,853 | 9/1976 | Morrizon | 602/36 |
| 4,328,794 | 5/1982 | Holmes | 602/5 |
| 4,476,857 | 10/1984 | Levine | 602/20 |
| 4,628,945 | 12/1986 | Johnson, Jr. | 602/13 X |
| 4,657,003 | 4/1987 | Wirtz | 128/869 |
| 4,911,152 | 3/1990 | Barnes et al. | 602/23 |
| 4,926,848 | 5/1990 | Shimkus et al. | 128/DIG. 15 |
| 5,101,815 | 4/1992 | Langdon-Orr et al. | 128/DIG. 20 X |
| 5,125,400 | 6/1992 | Johnson, Jr. | 602/13 |

FOREIGN PATENT DOCUMENTS

| | | | |
|---|---|---|---|
| 3826704 | 2/1990 | Germany | 602/23 |

Primary Examiner—Danton D. DeMille
Attorney, Agent, or Firm—Jerry Guenther

[57] ABSTRACT

The present invention is a new method for combining five fundamental methods of orthopedic immobilization into one multipurpose utility, integrated synergistic emergency spline (30) that operates using various integrated synergistic combinations of rigid fixation, soft fixation, inflation-actuated fixation, vacuum-actuated fixation, and traction-actuated fixation methods for strengthening and providing backup immobilization of each single method. Splint (30) is of layered design and function, comprised of an anatomically shaped unibody envelope (32) with a medial long axis monostay pocket (102) for retaining a removable central stiffening monostay (100), and a plurality of self-stowing, orbital compression, isokinetic tensing straps (34a–l) for circumferential closure. Contained within unibody envelope (32) is a stiffening framesheet (94) which provides shape, a malleable support platform, and energy transfer base for detachable traction system (71). Also within is a pliable pneumatic bladder (48) for inflation and vacuum functions, containing a plurality of expanded foam beads (60) that can be rigidified or free flowing for contour padding. Protruding from envelope (32) is a pneumatic control complex (52) which regulates pneumatic pressure with a control valve (74), and safeguards with a quantified pressure relief valve (66). Detachable traction system (71) functions using a kinetic extremity hitch (72) which is connected to a traction tensing harness (74a–b), and affixed to a traction bar (99) to provide dynamic traction when tensed. These layered components and systems combine to provide one multipurpose emergency unibody splint apparatus of dependable anatomic utilitarian design, that provide new integrated synergistic methods of orthopedic immobilization.

4 Claims, 14 Drawing Sheets

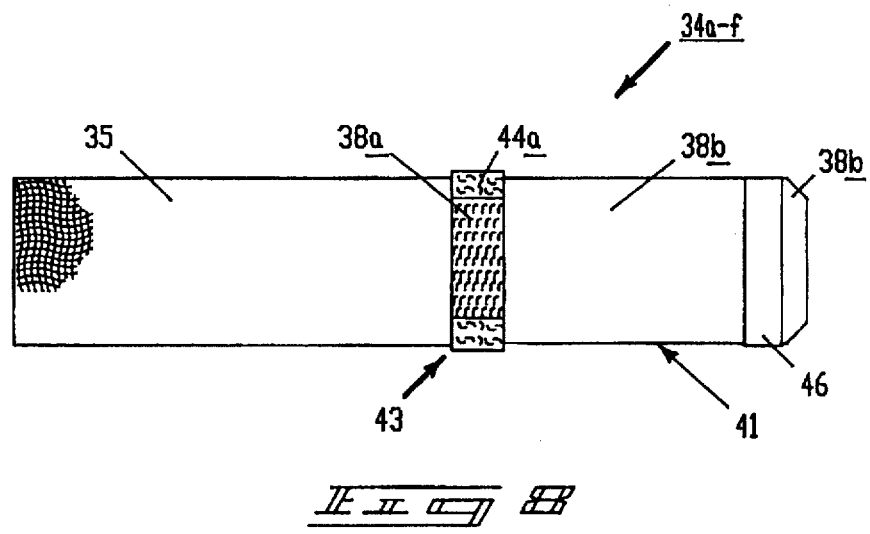
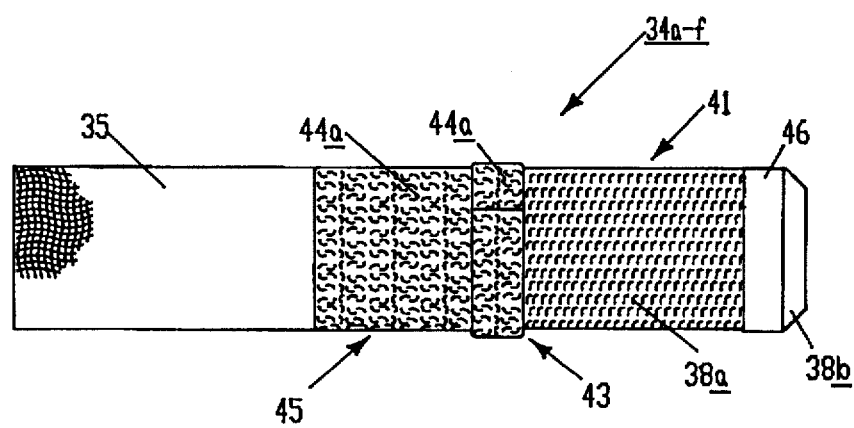

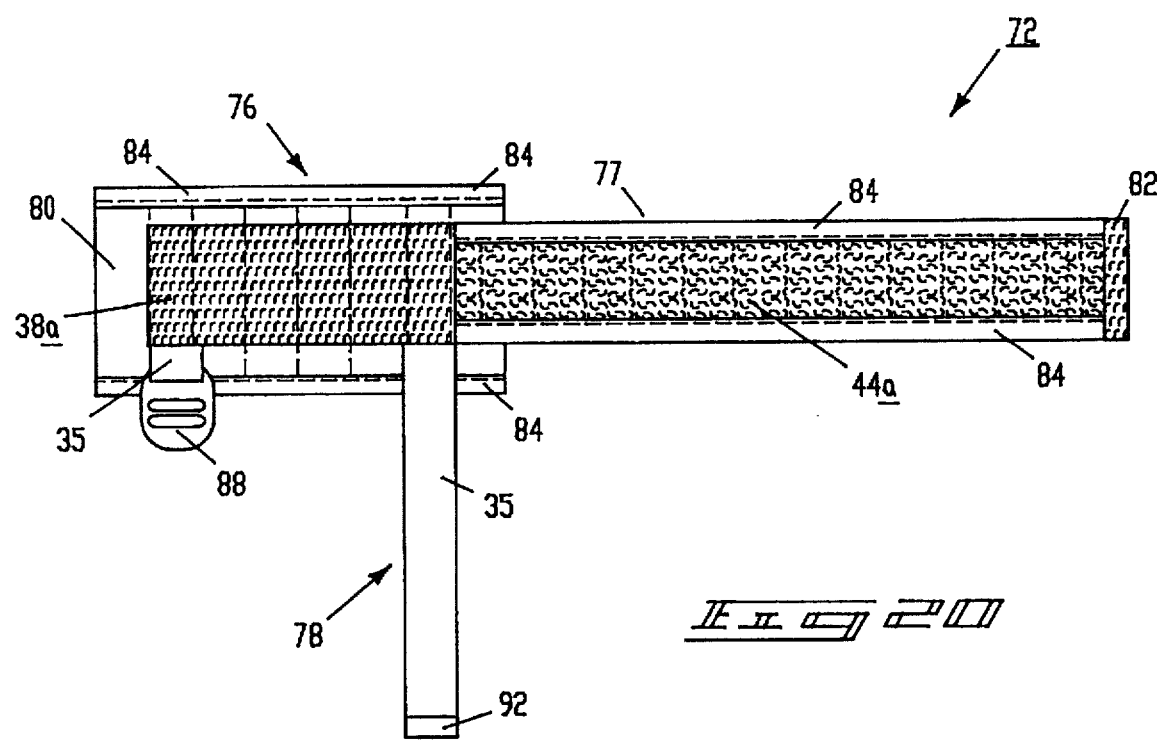
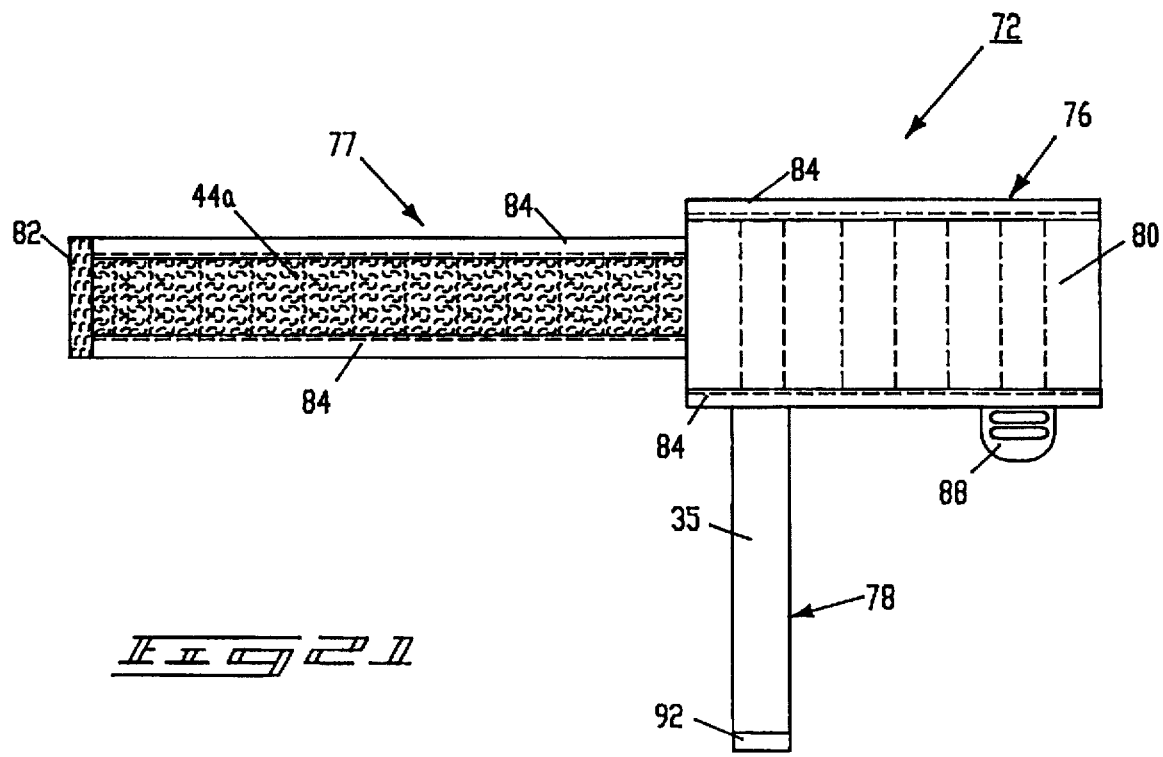

INTEGRATED SYNERGISTIC EMERGENCY SPLINT

This application is a continuation of application Ser. No. 08/054,639 filed Apr. 27, 1993, now abandoned which is a continuation of application Ser. No. 07/876,736 filed on Apr. 27, 1992, now abandoned.

BACKGROUND

1. Field of Invention

The present invention relates to splinting methods and apparatus used for emergency fracture immobilization and control of hemorrhage in a human's appendicular anatomy using fundamental orthopedic immobilization methods of rigid fixation, soft fixation, inflation-actuated fixation, vacuum-actuated fixation, and traction-actuated fixation in integrated synergistic combination.

2. Discussion of Prior Art

Musculoskeletal injuries are second in occurrence only to soft-tissue injuries. Splinting is an integral part of emergency field treatment of both musculoskeletal and severe soft-tissue injuries. A splint is defined here as an apparatus used to stabilize or immobilize a portion of a human's appendicular skeleton. A human's injured upper and/or lower extremity needs to be stabilized in a fixed physiologic position to allow for greatest comfort, adequate circulation, and efficient immobilization. This immobilization will prevent or reduce severity of secondary orthopedic musculoskeletal injury complications such as increased pain, soft-tissue damage, bleeding, restricted blood flow, and closed fractures becoming open fractures.

Heretofore, prior art splinting apparatus has been classified according to method of orthopedic immobilization implemented and structural design characteristics of apparatus. Prior art splints have been of single purpose utility for use with only one portion of anatomy and using only one method of orthopedic immobilization which is defined as soft fixation, rigid fixation, inflation-actuated fixation, vacuum-actuated fixation, and traction-actuated fixation.

In an attempt to locate prior art splinting apparatus that could provide integrated synergistic methods of orthopedic immobilization, none has been found available. However, U.S. Pat. No. 3,788,805 to Tourin, recognized general need for a traction-actuated splint to provide further extremity support in addition to known lateral and medial long axis longitudinal sustaining bars with cradles. Tourin provided this by using anterior and posterior detachable pneumatic cradles, which could also provide external pneumatic counter-pressure to assist in control of hemorrhage. The principle disadvantage is that should its environmentally exposed posterior detachable pneumatic cradle develop a leak or rupture, the injured extremity would be displaced posteriorly by the anterior pneumatic cradle and abandoned with no mechanism for support, leaving injured extremity elevated and suspended between proximal pelvic counter-traction rings and distal end traction tension bar and heel stand, allowing transmitted motion throughout injured extremity which could result in significant hemorrhaging and secondary musculoskeletal trauma to injured extremity. The Tourin splint is disadvantaged by its use limitation to only lower extremities and its performance ability when counter-pressure is medically contraindicated. In addition to its critical thermoplastic extremity support cradles being vulnerably exposed to rugged prehospital rescue environments.

There are an endless variety of prior art single purpose utility splints commercially available, with each having its own inherently unique disadvantages. Some of these splints are more suitable for certain kinds of extremity injuries than others. The particular method of splinting and kind of apparatus selected to immobilize an injured extremity depends upon a combination of injury location type of injury, kind of splint available, individual preference, and local medical protocols. The primary disadvantage of prior art single purpose utility splints is their inability to protect the well-being of an injured human in the event the splint experiences a catastrophic loss of immobilization, which could result in significant increases in pain, further soft-tissue damage, bleeding, restricted blood flow, and the possibility of a closed fracture becoming an open fracture.

Another disadvantage common to single purposes utility splints is that in order to provide the majority with a standard level of orthopedic care and immobilization, paramedical personnel need to be able to access a complete myriad of soft and rigid splints, inflation-actuated splints, vacuum-actuated splints, and traction-actuated splinting apparatus in a variety of adult and pediatric sizes. This myriad of splinting apparatus requires a considerable amount of emergency vehicle storage space, and adds to vehicle weight, which is critical to aeromedical evacuation. Often this space is not available or simple economics force compromise with regard to type and sizes of single purpose utility splints to be carried, leaving a void in paramedical field immobilization needs.

A precise working knowledge of this myriad of single purpose utility splints is extremely important. Every extremity injury is different, and each case will present different challenges to paramedical personnel, for splinting is not carried out in isolation, but rather must reflect the overall situation of the injured person. The original requisite of splint apparatus training and essential continuing educational requirements have real time and skill retention disadvantages from the standpoint of requiring proficiency with every single purpose utility splint carried, and having to maintain acceptable levels of field performance with each individual kind. The less paramedical proficiency and field performance maintained, the more length of time an injured person must spend at risk in the prehospital setting while awaiting transport to a definitive medical care facility.

Another disadvantage of single purpose utility splints is that once a decision is made as to the method and size of splint to be used, and the injured extremity is immobilized with that apparatus, the process is concluded. Should the injured person s condition change once the splint is applied, or paramedical assessment requires a non life-threatening change, it is not practical to remove that apparatus and reapply a more appropriate splint since less secondary musculoskeletal trauma is likely to occur if the injured person were left immobilized inappropriately than potentially could occur during an attempt to exchange splint apparatus.

The majority of musculoskeletal long bone extremity fractures or severe soft-tissue injuries are best cared for if they can be placed in a neutral anatomical position. Neutral positioning and alignment relieves tension on injured extremity ligaments and tendons. While manipulating extremity alignment is an uncomfortable process, it is necessary if prior art rigid splints, inflation-actuated splints, and traction-actuated splints are to be used in an efficacious manner. By their design structure and method of immobilization, they force alignment of the injured extremity, making it difficult to splint in any position other than aligned.

The rigid fixation splint is defined here as an inflexible, simple apparatus that can be constructed from any rigid object or material of proper size and shape, affixed to the injured extremity along one or both sides, front, or back to give stability. A primary disadvantage is that this kind of single purpose utility splint must be sell padded with foam or thick cloth to prevent pressure damage to superficial nerves and thin skin over bony projections, and to make adjustments for anatomical shape.

Another disadvantage is that a rigid fixation splint must be applied firmly enough to immobilized the injured extremity, but not so tight as to cut off circulation. When used with known circumferential binding materials such as unyielding tape, roller bandages, and cravats, the apparatus needs to be closely monitored by any loosening that may occur during transport, resulting in a loss of immobilization, and conversely for tightening that may occur from corollary swelling, resulting in circumferential vascular constriction to an already compromised area.

As the name implies, an initiation-actuated splint is a rigidified and collapsible support structure actuated by inflation with air or inert gas that grows rigid on the injured extremity, applying uniform circumferential immobilizing counter-pressure when inflated with sufficient pressure. The primary disadvantage that exists with all inflation-actuated splints is that when an air leak or decrease in pressure occurs from decrements in altitude or temperature, environmental punctures, needle sticks, deterioration of material or welds, valves or zippers, or material cracking under frigid conditions, the splint deflates and the injured extremity experiences a complete loss of immobilization, which could cause significant secondary musculoskeletal injury. Further, inflation-actuated splint's thermoplastic structure is vulnerably exposed to rugged prehospital rescue environments without any mechanism for protection of splint and injured extremity.

Another disadvantage of prior art inflation-actuated fixation splints is that when internal pressure within splint apparatus increases from atmospheric pressure change, significant rise in temperature, manual or mechanical pump over-inflation, it results in a traumatic circumferential counter-pressure being applied to an already vascular compromised injured extremity. Therefore, pressure within splinting apparatus must be checked frequently, carefully monitored after application at the scene, throughout surface or aeromedical transport, and after arrival at definitive care medical facility.

Another difficulty that exists with prior art inflation-actuated fixation splints is that the tube-like design structure must be applied by first sliding the apparatus over the applicator's upper extremity, which contaminates the splint, and than sliding apparatus onto the injured extremity like a sleeve, without any mechanism for long axis support. In addition, when the environment is warm, the injured extremity skin tends to stick to a thermoplastic surface during application and latter removal, which fixation splints with zippers can stick, clog with dirt, or freeze.

The traction-actuated fixation splint is simply a mechanical device used to counteract muscle spasms of an injured extremity and maintain the manual traction that is always a part of this immobilization process. It is intended to minimize secondary trauma to surrounding tissues, blood vessels, and nerves by immobilizing jagged and overriding bones ends by way of traction. Traction is a continuous long axis putting force, opposite to the pull of the major muscles, which promotes hemostasis, prevents shock, limits extremity movement, makes handling more efficient, and begins an important cycle of pain reduction and muscle spasm relaxation which results in the injured extremity anatomically lengthening.

The ischium has been used as a fulcrum for prior art traction-actuated fixation splints ever since they were developed by Lardenois and Thomas in the late 1800's, and has not changed since then. Commercial splint-makers have concentrated on improving harness systems, proximal ischial or perineal bar cushioning, and framework adjustability. When traction-actuated splints apply traction to the distal lower extremity through an anide hitch, a force is exerted by the upper proximal end of the splint against the pelvis. This force is called countertraction. All traction-actuated fixation splints are dependent on a countertraction force for immobilization, and without that force immobilization ceases. Prior art traction-actuated splints must be well seated anatomically on their designed proximal pelvic contact point for effective countertraction. Because prior art traction-actuated fixation splints must be sealed against a proximal arch type anatomic structure, they are not suitable for use on upper extremities because countertraction forces cannot be tolerated by major nerves and blood vessels in the axilla.

When countertraction is applied against the ischial tuberosity and/or ischium by a prior art traction-actuated fixation splint there are other disadvantages. In spite of greater flexion of the lower limb there is still too much variation in height requirement for the fixed ischial bar to be always in the correct location impinging on the ischial tuberosity. The ischial and/or perineal bar needs to be padded for comfort, especially to avoid excessive pressure on external genitalia, but if due to excessive padding on an ischial bar, or if too much elevation of the ischial bar occurs, an upward force is applied to femur proximal bone fragment that may project it upward into the soft tissue above. This can cause further musculoskeletal injury, particularly in cases where proximal fragment is shorter than one-third the length of the femur. If there is not enough elevation of the ischial bar when countertraction is applied, it will not actually engage the ischium and will slip upward, reducing or causing a sudden loss of traction.

Traction-actuated splints are generally used on isolated mid-shaft lemur fractures of person's who present without hemodynamic embarrassment. Traction splints are not designed to be used when a person is suspected of having an associated fracture of the pelvis, or a hip injury with gross displacement, or if suspected fracture is within 2" to 3" inches of knee, or if any significant injury to the knee is present, or when fractures are suspected in the lower third of the leg, especially at or near the ankle. Without x-rays, it is impossible to distinguish joint injuries from breaks, and prior art traction could cause joint damage, therefore another kind of splint must be utilized for immobilization.

Single purpose utility splints that maintain musculoskeletal anatomy in position found, are utilized when neutral positioning and alignment could produce unwarranted pain and secondary trauma to the injured extremity, or where medically contraindicated by location of fracture, as in close proximity to a join, or a joint dislocation has occurred. Under these circumstances the injured extremity is immobilized very differently. Soft fixation or vacuum-actuated fixation splints have the ability to conform to an angulated injured extremity, and immobilize in a found position.

A vacuum-actuated splint is a rigidified and collapsible splint that when applied follows the contour and bands of the injured extremity while in a collapsed and pliable state. When residual air is evacuated with a mechanical vacuum pump, its polymer beads are drawn closer together and compressed encasing injured extremity with little or no circumferential pressure, leaving the vacuum-actuated splint rigid and cast-like in the anatomical position of application. The primary disadvantage that exists with all prior art vacuum-actuated fixation splints is that when a vacuum leak or equalization of atmospheric pressure occurs from increments in altitude or temperature, exposure to environmental punctures, deterioration of material or welds, valve failure, or cracking of fabric coating under frigid conditions, the splinting apparatus softens and the injured extremity experiences a complete loss of immobilization, it could cause significant secondary neurovascular and/or musculoskeletal injury. Therefore, rigidity of splinting apparatus must be checked frequently and carefully monitored after application to assure effective immobilization is maintained at the scene, and throughout surface or aeromedical transport to a definitive medical care facility.

Another disadvantage of prior art vacuum-actuated fixation splints is that during application of apparatus in its collapsed state, there is no mechanism for support of the injured extremity other than manual hands-on support of multiple paramedical personnel, which could unintentionally, through lack of communication or maneuvering room, induce painful extremity manipulation generating secondary musculoskeletal trauma. Further disadvantages occur once the splint is wrapped around the injured extremity since there is no mechanism for maintaining uniform circumferential application compression pressure during air evacuation, which is necessary for the immobilizing polymer beads to flow into anatomical voids, rather than voids created by splint apparatus. When prior art vacuum-actuated fixation closure straps are applied before air-evacuation, apparatus voids are created as closure straps loosen from contraction of splint, negating any static strap closure pressure previously applied, making it necessary for the static straps to be removed and reapplied to maintain a sufficient closure pressure.

A soft fixation splint, as the name implies, is made of relatively soft material and is usually applied around the injured extremity, generally remaining somewhat flexible after application. This kind of soft fixation splinting includes age old sling and swathe immobilization methods, metal wire ladder splints, malleable aluminum splints, and any improvised soft splint made from available materials such as folded parkas, blankets, or pillows. The major disadvantage of soft fixation splinting is that it does a poor job of fully immobilizing the injured extremity's joints above and below the injury site, leaving much of the effectiveness of soft splinting dependent on the injured person's cooperation. Another disadvantage of the soft splint is that it must be applied firmly enough to secure the injured extremity with circumferential binding materials such as tape or cravats which are difficult to adjust once applied, and difficult to judge the correct amount of application tension required due to malleable apparatus surfaces, which could result in a loss of immobilization during movement of injured extremity.

It will now be apparent that a need exists for a comprehensive emergency splint which has integrated synergistic orthopedic immobilization capabilities that aid in the protection and well being of injured persons, is sufficiently compact, and capable of being applied quickly and safely by a person with little or no previous experience, without further aggravating an already traumatized condition.

OBJECTS AND ADVANTAGES

While numerous splints for human use have been available for many years, there are still adequate regions for improvement. The present invention has been developed after much research and study to provide persons suffering from orthopedic injuries with a margin of safety and comfort necessary to aid in prevention of secondary injury and pain. Accordingly, the object of present invention is to provide an integrated synergistic emergency splint of dependable anatomic multipurpose utilitarian design that incorporates the five fundamental orthopedic methods of splint fixation in various synergistic relationships, in one integrated emergency unibody splint apparatus, with layered components working together to provide unequaled safeguarding and comfort, improved immobilization, enhanced reliability with rapid, versatile, ergonomic apparatus utilization.

The present invention is believed to be far superior to any temporary or emergency splint now in existence because it contains a plurality of soft fixation, rigid fixation, inflation-actuated fixation, vacuum-actuated fixation, and traction-actuated fixation methods which may be used in various combinations, symbiotically assisting one another in immobilization, and delivering backup immobilization in the event one of the combined methods experiences a mechanical failure. Another object of this unique present invention includes replacement of live single purpose utility splints with only one multipurpose unibody splint, thereby saving considerable storage space and reducing weight in emergency vehicles, especially air ambulances, providing less paramedical training time while increasing skill retention time, in addition to reducing cost or procurement without loss of capability. A further advantage is that present invention may be used for more than one portion of the appendicular anatomy, with capacity to vary its multipurpose functions, efficaciously immobilizing numerous types of orthopedic and soft tissue injuries.

Another object of this present invention is to satisfy a real tangible need for an integrated synergistic emergency splint which is inexpensive and within budget possibilities of organizations most needing them, that is volunteer organizations of first responders who provide prehospital emergency paramedical care and rescue who usually do not have means, economic or otherwise, for having available multiple kinds and sizes of single purpose utility splints. The present invention envisions use by non-ambulance types such as law enforcement services, ski patrols organizations, fire rescue services, event emergency standby services, industrial and sports medicine technicians, and other first responders. With the object being to supply every prehospital emergency paramedical care and rescue provider with a multipurpose integrated synergistic emergency splint that is capable of being safety applied in seconds, without risk of further injury or damage to the injured person, by a lay person with little previous experience in immobilization, which circumferentially cradles injured extremity as a unit, rendering fractured portions immobile, and is comfortable enough to be left on for long periods of time without vascular compromise, pressure points, or nerve compression.

Another advantage of present invention is that it can provide a majority of injured persons with a standard level of orthopedic care and immobilization by providing paramedical personnel with an inexpensive, multipurpose utility integrated synergistic emergency splint that serves both adult and pediatric, is ultra lightweight, and requires very little emergency vehicle storage space. Orientation training on present invention and required continuing education has real time and skill retention advantages from the standpoint of having to become proficient with only one multipurpose utility emergency splint. Prehospital emergency paramedical care and rescue is often practiced in an extremely distracting, rugged, and sometimes hostile environment making it absolutely essential for an easy to use, integrated synergistic emergency splint that can be positively applied in seconds, and more importantly safeguards the injured person. The military is especially in need of an integrated synergistic emergency splint such as this. The present invention allows paramedical personnel to concentrate on rendering care for their injured, rather than managing orthopedic splint apparatus.

Another important advantage of multipurpose present invention is that it is not necessary to access the injured person before knowing what kind of splint to take. This is especially important in wilderness rescue, armed service front-line evacuation and large catastrophic accident or natural disaster first-aid responses. It is also desirable for institutions and industries desiring self-contained first aid equipment with multiple capabilities. A similar advantage is the capability of present invention to be applied quickly for rapid evacuation using only the rigid and soft fixation methods, and then adding appropriate traction, inflation or vacuum-actuated fixation later when situation permits, without having to remove splint apparatus.

The present invention furnishes paramedical personnel with the advantage of selecting the method of immobilization to be used at the injured person's side, and should person's condition or needs change, the method of immobilization can be changed without having to return to the emergency vehicle or remove the integrated synergistic emergency splint. An example being a person who was immobilized by a traction/vacuum-actuated fixation method that applies little external circumferential pressure, and latter during transport this person starts to hemorrhage. Now vasoconstrictive external counter-pressure is required to tamponade bleeding, and vacuum-actuated fixation can be replaced with inflation-actuated counter-pressure without loss of traction-actuated immobilization. In other instances, if paramedical technician wanted to eliminate use of pneumatics, this injured person would continue to experience traction-actuated immobilization with rigid and soft fixation circumferential support.

The present invention is of layered integrated unibody structure which is inexpensive to manufacture, ultra lightweight, with all components being replaceable, easily cleaned and decontaminated, yet rightly efficient in accomplishing its multipurpose synergistic immobilization objective. This is a real contribution to prehospital emergency paramedical care and rescue. The principle advantage of layered unibody construction is that all vulnerable and critical components of the integrated synergistic emergency spirit are protected from commonplace prehospital environmental exposures. Another features of this present invention is that all hardware and soft goods are constructed of non-metallic or non-ferrous material, such as urethane, latex, polyester, nylon, acetal, aluminum and carbon fiber reinforced plastic materials. Use of these materials has allowed X-ray photographs, CAT scans, and MRI scans to be taken with splint still in position since these materials will not interfere with this type of diagnostic testing.

Another advantage of present invention is the incorporation on unibody envelope of self-slowing, orbital compression, isokinetic tensing straps which are applied manually to maintain a constant closure tension through expansion or retraction in response to increased or decreased pressure on injured extremity. Another advantage is the capacity of isokinetic tensing straps to automatically adjust, making strap readjustment unnecessary by maintaining a constant closure tension on splint apparatus as circumferential shrinkage occurs during application of vacuum-actuated fixation. Similarly, the detachable traction system includes a mechanism for applying dynamic traction pull to musculoskeletal tissues that self-adjusts through expansion and retraction as muscles spasm and relax.

Another advantage of present invention is its ability to provide the injured extremity with an immediate long axis planar support platform from which quick rigid and soft fixation is launched by simple closure of self-stowing, orbital compression isokinetic tensing straps. Another object of present invention is to provide improved total injured extremity support. This is accomplished by circumferentially encasing injured extremity with a layered unibody envelope that contains a resilient stiffening framesheet for malleable firm support and expanded foam beads for soft contoured padding, a central stiffening monostay for rigidity, and isokinetic tensing straps for maintaining a desired constant closure tension. Still another advantage of present invention is that isokinetic tensing straps are self-stowing, can be applied, removed, and returned to their ready storage position using one quick simple motion. This self-stowing method eliminates premature engagement of straps to foreign materials such as carpet and clothing during application of the splint, and provides a method for protecting the strap tip from picking up foreign materials such as fabric lint, dirt, and grass prior to application.

Still another object of present invention is to safeguard the injured extremity by providing environmental protection for vulnerable pneumatic bladder, and should a loss of inflation occur for any reason ensure both rigid and soft fixation remain as backup systems in the integrated synergistic emergency splint. The pneumatic bladder's first line of defense is an extremely tough, fluid immune, tear and abrasion resistant unibody envelope, firmly supported by a protective shock absorbing, puncture resistant stiffening framesheet. Another advantage is that the injured extremity is protected further from excessive vascular constriction by providing a preset automatic pressure relief valve that prevents inflation pressures above Academy of Orthopedic Surgeons recommended 40 millimeters of mercury, and provides a quantifiable mechanism for testing for sufficient inflation pressure, and excessive circumferential application pressure.

Another advantage of the multipurpose integrated synergistic emergency splint is that it provides a long axis malleable support base for stabilizing an angulated extremity while waiting for the vacuum rigidity to be actuated. This is accomplished by simply removing the central stiffening monostay from is pocket. More importantly, the integrated synergistic emergency splint retains its soft fixation support base should vacuum rigidity be lost for any reason, without the injured extremity suffering a complete loss of immobilization.

Another object of present invention is to provide a synergistic traction-actuated fixation splint that is not dependent on a specific point of anatomy proximal to splint from which to generate countertraction. This translates to fewer pounds per square inch of pressure on any one part of the injured extremity or other anatomy, which means less pain and greater splint stability. Not only was it an object to provide posterior extremity support, but it was found advantageous to provide circumferential support that uniformly applies pressure to entire injured extremity, providing extraordinary splint stability and transfer of pressure. This circumferential support system allows use on upper extremities, as well as on person's suspected of having associated fractures of the pelvis, or grossly displacement hip injuries, or suspected fractures within 2 to 3 inches of knee or when any significant injury to the knee was present, or when fractures were suspected in the lower third of the leg, especially at or near the ankle.

Another object of present invention is to provide a kinetic extremity hitch that when tensing delivers an extremely comfortable and anatomically correct, in-line dynamic force that insures against loss of traction from anatomic locomotion of spastic muscle contraction and relaxation elongation phases that naturally occur in injured extremities. An advantage of present invention is that tension is produced and controlled by a manual traction tensing strap which is easy to use, simple to release, and constructed to eliminate dangers of accidental release, yet provides the paramedical technician with infinitely minute increments of traction tension adjustment in both directions, either toward or away from injured extremity, making transition from manual traction to mechanical traction a fluid process.

The integrated synergistic emergency splint is a new splint apparatus, with new methods for orthopedic immobilization that improve on all prior art single purpose utility splints by using known single purpose utility orthopedic immobilization methods in new integrated combinations to form new synergistic methods of orthopedic immobilization that are delivered in one multipurpose innovative unibody immobilization splint with no known disadvantage.

BRIEF DESCRIPTION OF DRAWINGS

The present invention is better understood by reference to the following descriptions, when used with accompanying drawings, in which:

FIG. 8 is a top plan view of isokinetic tensing straps 34a–l, in an extended position of use, as illustrated in FIG. 4;

FIG. 9 is a bottom plan view of isokinetic tensing straps 34a–l, as shown in FIG. 8;

FIG. 20 is a top plan view of extremity hitch 72 outer face, illustrated in a planar position;

FIG. 21 is a bottom plan view of extremity hitch 72 inner face, as shown in FIG. 20;

REFERENCE NUMERALS

Figure 1:
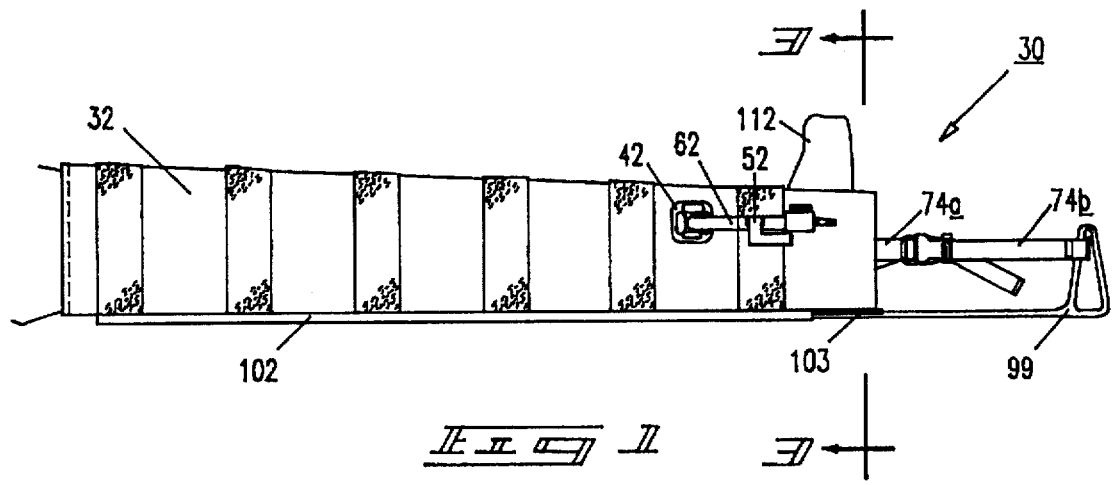
FIG. 1 is a side elevation view of integrated synergistic emergency splint 30, illustrating side with pneumatic control complex 52, when applied to a human lower extremity 112 and immobilized with an integrated synergistic traction-actuated fixation method.

| Reference Numerals | | | |
|---|---|---|---|
| 30 | Integrated Synergistic Emergency Splint | 45 | Tip Storage Pad |
| 32 | Unibody Envelope | 46 | Ultrasonic Weld |
| 34a-l | Isokinetic Tensing Straps | 48 | Pneumatic Bladder |
| 35 | Elastic Material | 50a-c | Expansion Containment Walls |
| 36 | Outer Sheet | 52 | Pneumatic Control Complex |
| 37 | Inner Sheet | 54 | Radio Frequency Heat Seal |
| 38a | Hook Tape Engaging Front | 56 | Bladder Front Panel |
| 38b | Hook Tape Back | 57 | Bladder Back Panel |
| 39 | Pocket Reinforcement | 58 | Vinyl Coated Nylon Mesh Fabric |
| 41 | Strap Tip | 59 | Vinyl Coated Nylon Fabric |
| 42 | Elastomer Lash Tab | 60 | Expanded Foam Beads |
| 43 | Seam Cover Engagement Band | 61 | Truncated Angle Connector |
| 44a | Loop Tape Engaging Front | 62 | Angle Connector |
| 44b | Loop Tape Back | 63 | Angle Connector Filtration Screen |
| 64 | Control Valve | 88 | Ladder Locking Buckle |
| 65 | Round Valve Handle | 90a | Side Release Male Buckle |
| 66 | Pressure Relief Valve | 90b | Side Release Female buckle |
| 68 | Insert Tee | 92 | Web Belting |
| 70 | Tubing Segment | 94 | Stiffening Framesheet |
| 71 | Detachable Traction System | 96 | Closed-Cell Foam |
| 72 | Extremity Hitch | 98 | Traction Bar Assembly |
| 74a-b | Traction Tensing Harness | 99 | Traction Bar |
| 76 | Contact Pad | 100 | Central Stiffening Monostay |

-continued

| Reference Numerals | | | |
|---|---|---|---|
| 77 | Envelopment Band | 102 | Monostay Pocket |
| 78 | Kinetic Tensing Strap | 103 | Pocket Tip |
| 79 | Urethane Coated Nylon Fabric | 106 | Graphite Fiber |
| 80 | Urethane Coated Polyester Fabric | 108 | Mold Mask |
| 82 | Extruded Hook Tape | 110 | Monostay Stop |
| 84 | Binding Tape | 112 | Human Lower Extremity |
| 86 | Simple Connecting Loop | | |

DETAILED DESCRIPTION OF PREFERRED EMBODIMENT

Figure 2:
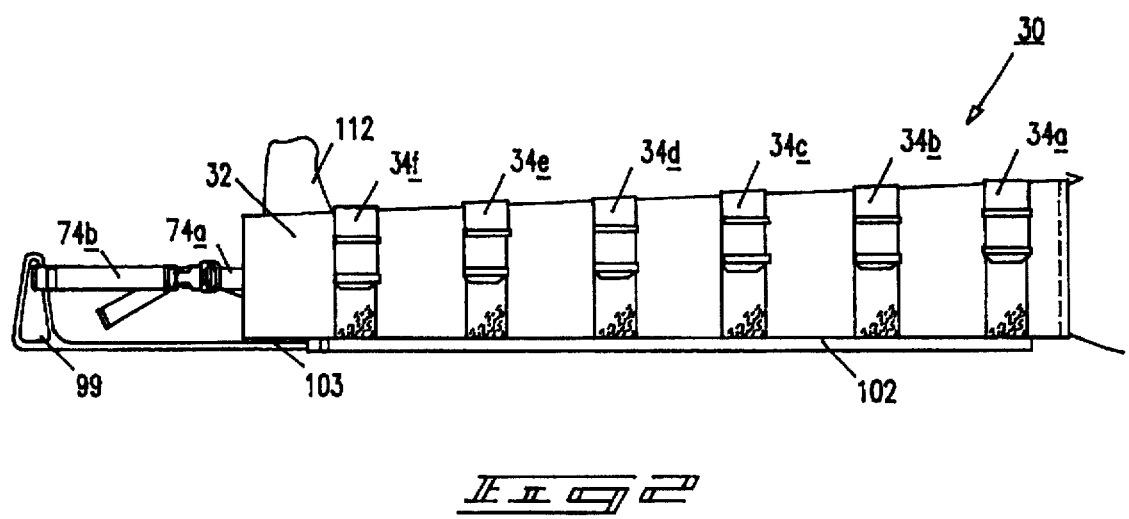
FIG. 2 is an opposing side elevation view of FIG. 1, illustrating integrated synergistic emergency splint 30, isokinetic tensing straps 34a–l, when applied to a human lower extremity 112 and immobilized with an integrated synergistic traction-actuated fixation method.
Figure 3:
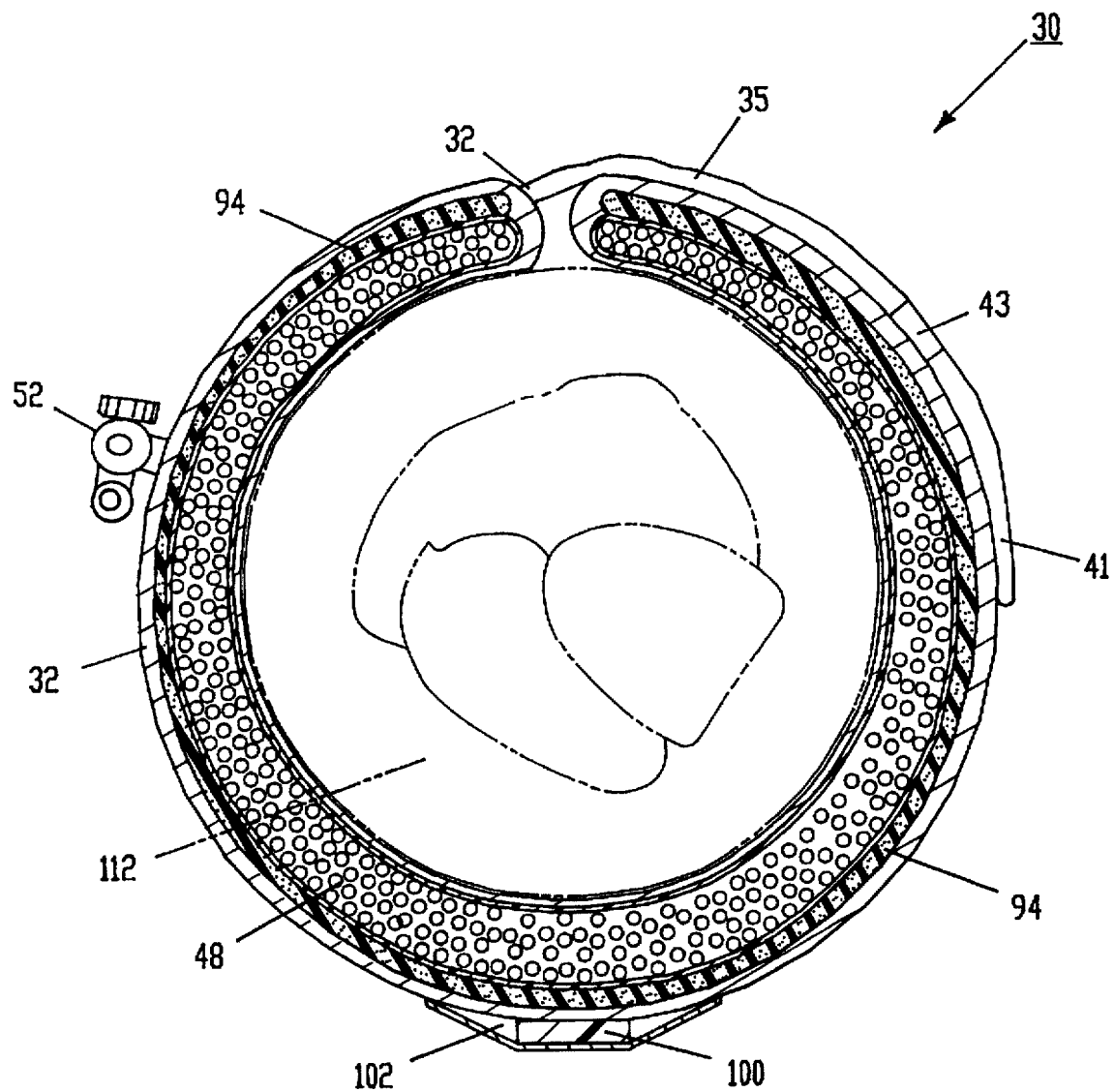
FIG. 3 is a simplified cross-sectional view of integrated synergistic emergency splint 30, illustrating relative position of apparatus components as configured on a human lower extremity 112.

FIGS. 1 to 3: Application Views

FIGS. 1, 2 and 3 shown three different views of integrated synergistic emergency splint 30 attached to a human lower extremity 112. Unibody cover or envelope 32 contains within its enclosures a stiffening framesheet 94, a pneumatic gag or bladder 48 containing expanded foam beads 60 with a protruding pneumatic control complex 52, central stiffening monostay 100, and attached to it a detachable traction system 71. These components and systems combine in a manner providing safety through integrated fixation methods, consisting of rigid fixation, soft fixation, vacuum-actuated fixation, inflation-actuated fixation, and traction-actuated fixation methods, as well as improvement of each individual method through synergistic fixation support of other methods. Preferred embodiments shown in FIGS. 1 through 3 are described in detail in following figures and descriptions.

FIGS. 4 to 11: Unibody Envelope Views

Unibody envelope 32 is a trapezoid shaped bag, conforming to general anatomical shape of human extremities, with self-stowing, orbital compression isokinetic tensing straps 34a-l attached. Envelope 32 and encased components combine to contribute comfort, protection and circumferential long axis fixation to all portions and surfaces of an injured extremity.

Figure 4:
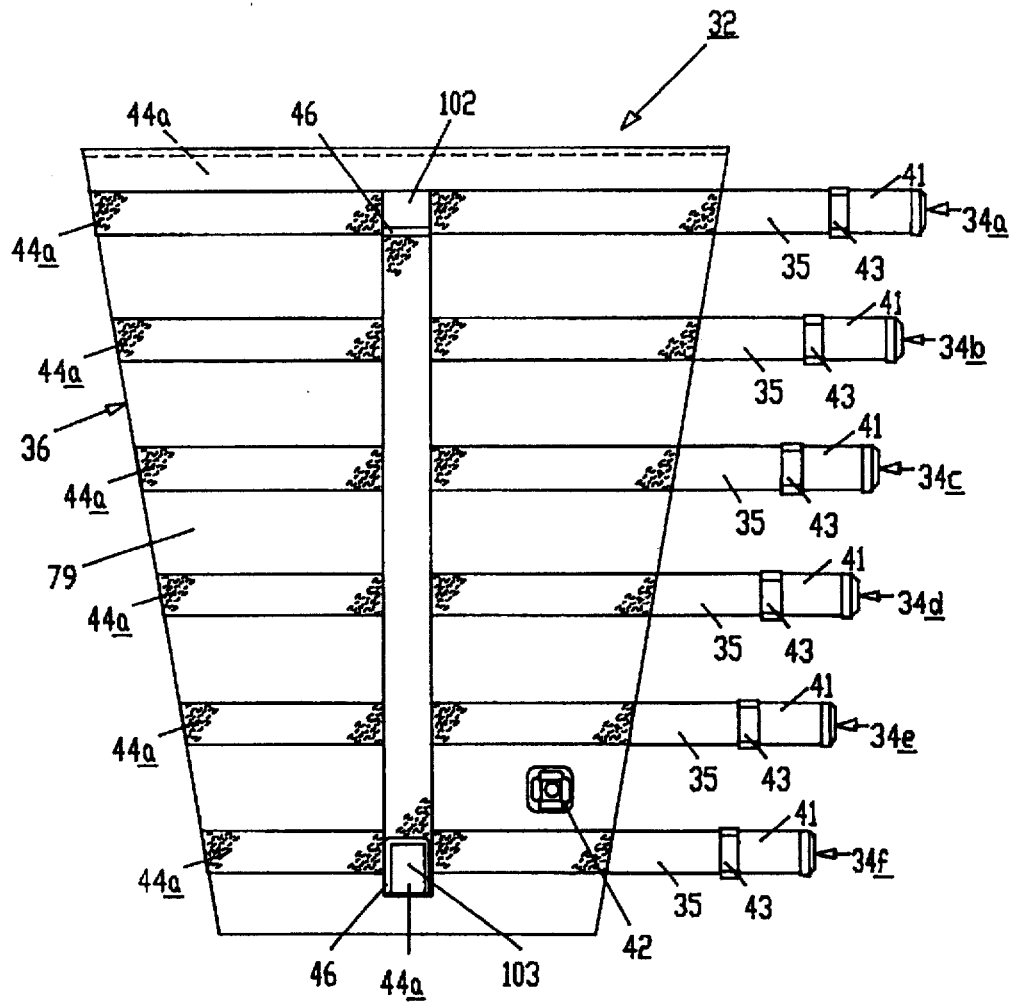
FIG. 4 is a top plan view of unibody envelope 32 outer sheet 36, shown planar with isokinetic tensing straps 34a–l *in an extended position of use;*
Figure 5:
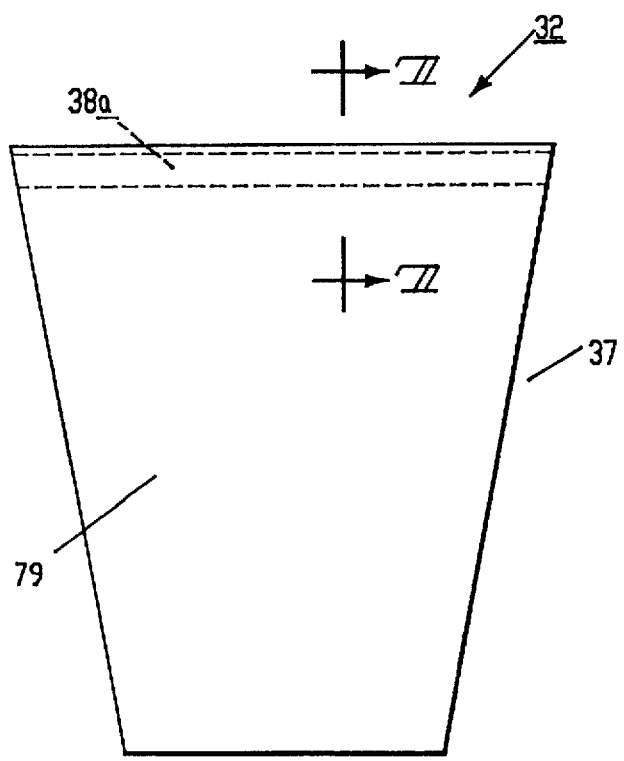
FIG. 5 is a top plan view of unibody envelope 32 inner sheet 37.

FIG. 4 snows outer sheet 36 of envelope 32 with attached straps 34a-l, which will be described in FIGS. 8 and 9. Sheet 38 is non-abrasive, finely woven coated fabric with high tear strength and excellent fluid immune properties, such as a preferred urethane coated nylon fabric 79. Inner sheet 37 shown in FIG. 5 is a very similar urethane coated nylon fabric 79 with less urethane coating than outer sheet 36 which helps to communicate a more pliable surface texture to injured extremity.

Figure 10:
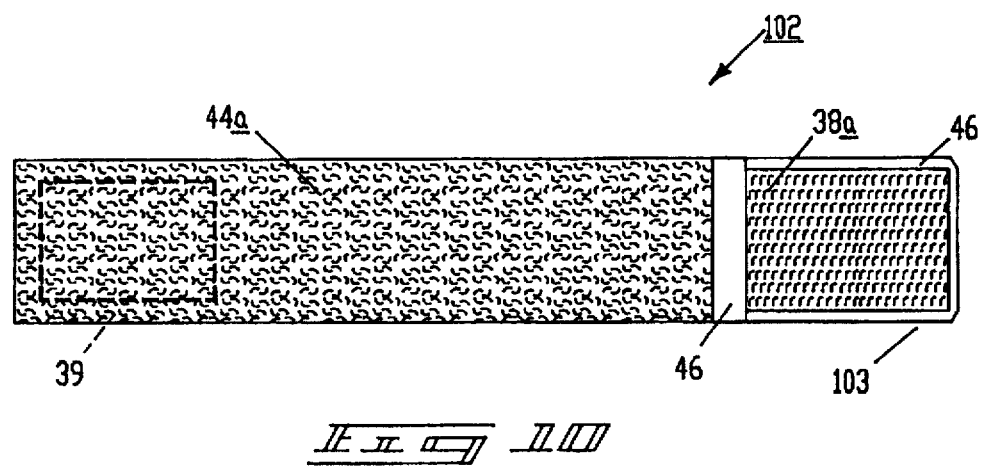
FIG. 10 is a top plan view of monostay pocket 102, with pocket tip 103 in an extended open position.
Figure 11:
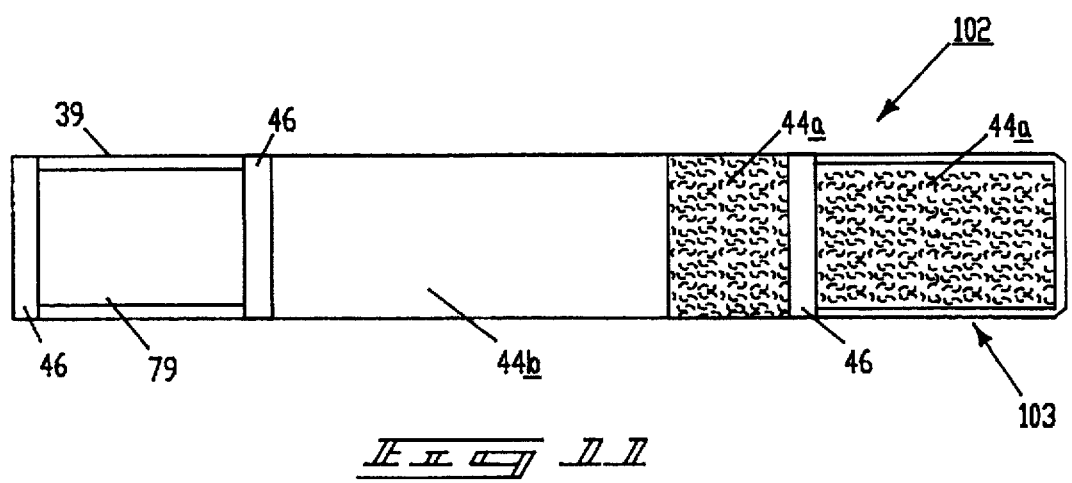
FIG. 11 is a bottom plan view of monostay pocket 102, as shown in FIG. 10.

FIG. 4 also shows loop tape engaging front 44a bands sewn at regular intervals from side to side of sheet 36, parallel with wide proximal base and distal top, designed to receive hook strap tip 41 during circumferential application to injured extremity. Monostay pocket 102 shown in FIG. 4 is a strip of loop tape 44a, as shown in FIGS. 10 and 11, with pocket reinforcement 39 at wide proximal base end, and pocket tip 103 at distal end. Preferred reinforcement 39 is nylon fabric 79; preferred tip 103 is hook tape engaging front 38a. Pocket 102 is formed by sewing doubled-over reinforcement 39 to make a closed pocket end at center of loop band 44a nearest wide proximal base closure end of envelope 32, leaving opposing distal end open for closure by tip 103. Reinforced end of pocket will retain mold mask 106 end of monostay 100 when installed, and closure tip 103 will prevent movement or less of monostay 100 when closed.

Elastomer lash tab 42 is shown sewn directly over circular opening in sheet 36, providing wear point protection, and stabilizing locus for urethane angle connector 62.

Figure 7:
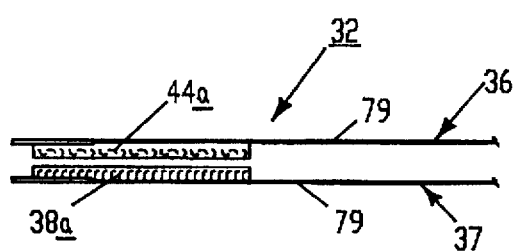
FIG. 7 is an exploded longitudinal section view of unibody envelope 32, illustrating preferred embodiment method of closure of out sheet 36 and inner sheet 37.

FIG. 7 shows preferred closure method for opening in envelope 32 at wide proximal base end of trapezoid. Raw edge of sheet 36 is hemmed and loop tape 44a is sewn on as shown; similarly, sheet 37 and hook tape 38a is installed to create a preferred method of closure for envelope 32. Assembly of envelope 32 requires sheet 36 and 37 to be placed together with their exterior surfaces in contact with straps 34a-f placed onto and aligned with loop tape bands 44a in such a manner that elastic material 35 ends abut side perimeter closest to tab 42 of positioned sheets 36 and 37. Sheets 36 and 37 and straps 34a-f are then sewn together along one side, and only sheets 36 and 37 are sewn together along perimeters of opposite side and distal top of trapezoid, leaving wide proximal base end of trapezoid open. Sewn seams are then finished with single-fold nylon binding tape 84 sewn over raw edges to reinforce and seal seams, preventing fabric separation during utilization, cleaning and drying processes. Envelope 32 is then turned inside-out to expose exterior surfaces of envelope 32 as shown in FIG. 4. Completed envelope 32 is essential base component of present invention since all other parts are contained within it, on it or attached to it.

Figure 6:
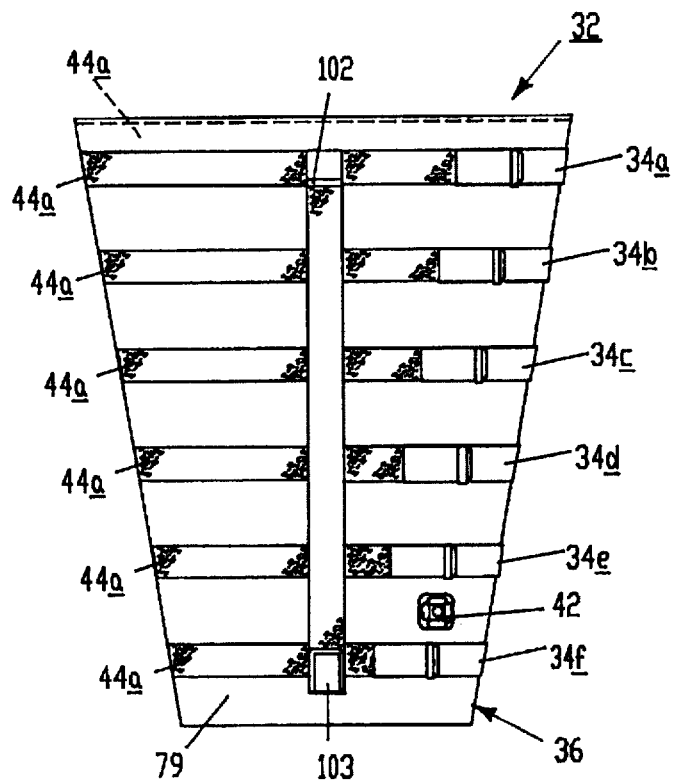
FIG. 6 is a top plan view of unibody envelope 32 outer sheet 36, as shown in FIG. 4, with isokinetic tensing straps 34a–l in a retracted self-stowing position.

FIG. 6 shows completed envelope 32 with straps 34a-l folded back upon loop tape 44a bands in an easy application storage position, thereby preventing hook tape 38a of tip 41 prematurely engaging foreign materials during application process and allowing simple, quick, one movement operation of straps 34a-l to tape 44a from easy application storage position.

FIG. 8 shows preferred embodiment of top view of straps 34a-l wherein tip 41 consists of hook tape back 38b sewn to elastic material 35, with seam cover engagement band 43 box stitched over this union. Band 43 consists of a band of loop tape 44a with a piece of hook tape 38a not longer than width of elastic material 35 affixed parallel by ultrasonic weld 46 to center of band 43, and then entire band 43 is box stitched to seam. Preferred elastic material 35 has heavy duty 50% elasticity which assures continuous isokinetic adjustment and closure tension of splint 30 by self-stowing, orbital compression isokinetic tensing straps 34a-l.

FIG. 9 shows preferred embodiment of back view of straps 34a-l wherein tip storage pad 45, consisting of loop tape 44a, is sewn to elastic material 35 immediately adjacent to band 43. Tip 41 is folded over upon itself and affixed with weld 46 to form non-engaging apex for gloved hands to grip during paramedical application and removal processes. Easy application storage position of strap 34a-l is accomplished by folding tip 41 over to engage loops on storage pad 45, and then folding in a reverse direction to secure band 43 hooks to tape 44a loop bands sewn on sheet 38, as shown in FIG. 6.

FIGS. 12 to 18: Envelope Component Views

Figure 12:
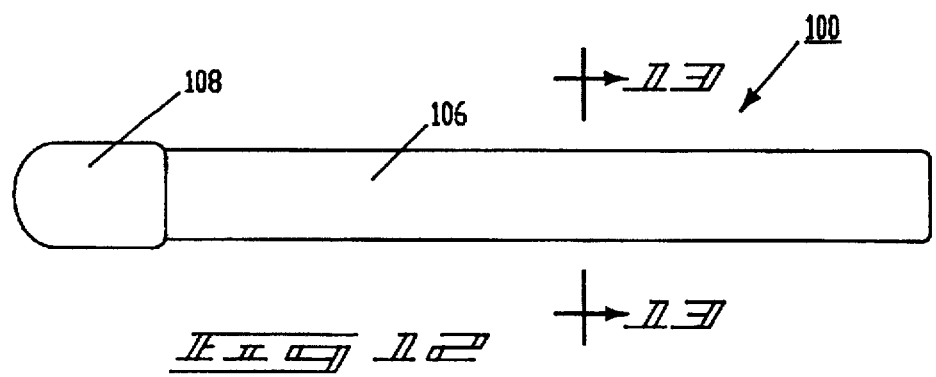
FIG. 12 is a top plan view of central stiffening monostay 100, illustrating a tube structure with one end protected with mold mask 108.
Figure 13:
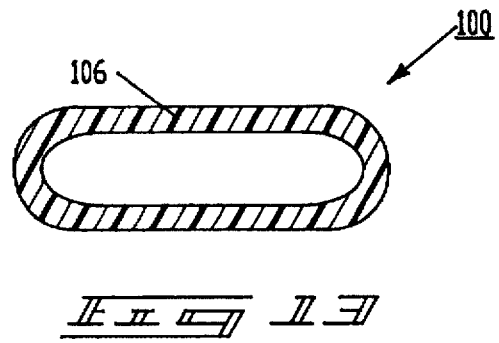
FIG. 13 is a cross sectional view of central stiffening monostay 100.

FIG. 12 shows abbreviated central stiffening monostay 100 with attached mold mask 108. Preferred embodiment is a reinforce unidirectional graphite fiber 106 pultruded roving polyester resin matrix tube that provides for radiographic clarity, increased strength and rigidity. Monostay 100 is designed to provide strength with marginal flexural properties when providing traction-actuated fixation, and to provide rigidity when used without traction.

Figure 14:
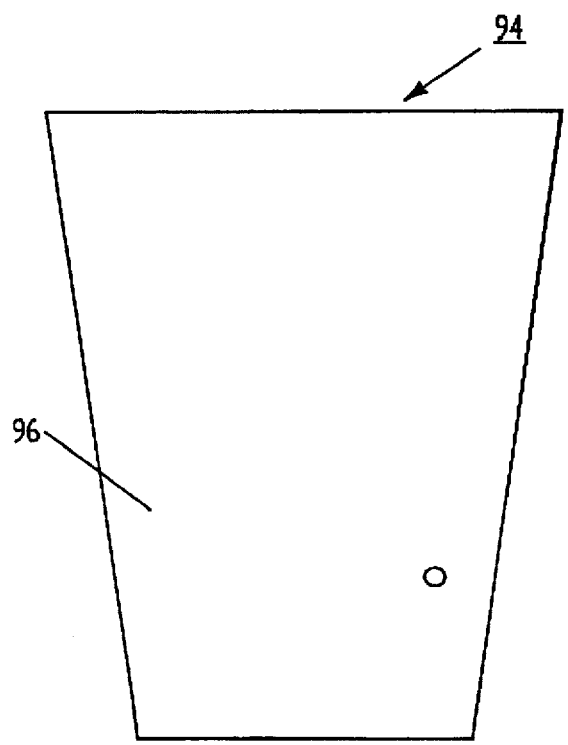
FIG. 14 is a top plan view of stiffening framesheet 94.

FIG. 14 shows stiffening framesheet 94 which is composed of closed-cell foam 96. Preferred embodiment is a micro-cellular high density close-cell expanded polyethylene vinyl acetate material which has desirable ultra lightweight properties, has responsive memory, is impact resistant, x-ray transparent, and has easily cleaned fluid immune surfaces. Preferred even thickness of framesheet 94 is 7 millimeters. Framesheet 94 provides soft fixation by uniformly stiffening and providing malleable frame for envelope 32, supportive enough to provide injured extremity with a structural long axis support base and supply lateral planar surface for protection of pneumatic bladder 48 from environmental harm, and aid in smooth flow of expanded foam beads 60 to anatomically void areas upon application.

Figure 15:
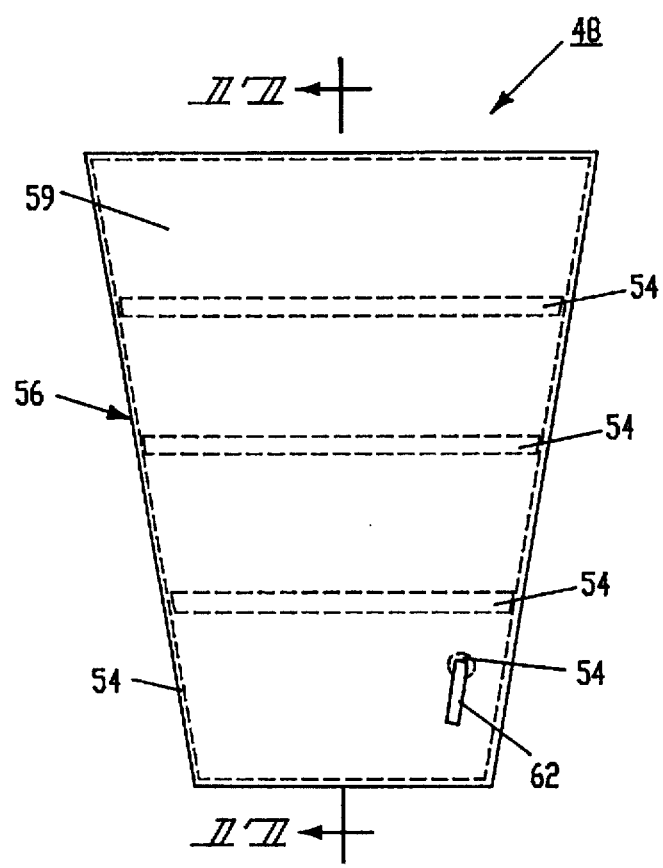
FIG. 15 is a top plan view of pneumatic bladder 48, bladder front panel 56, showing angle connector 62.
Figure 16:
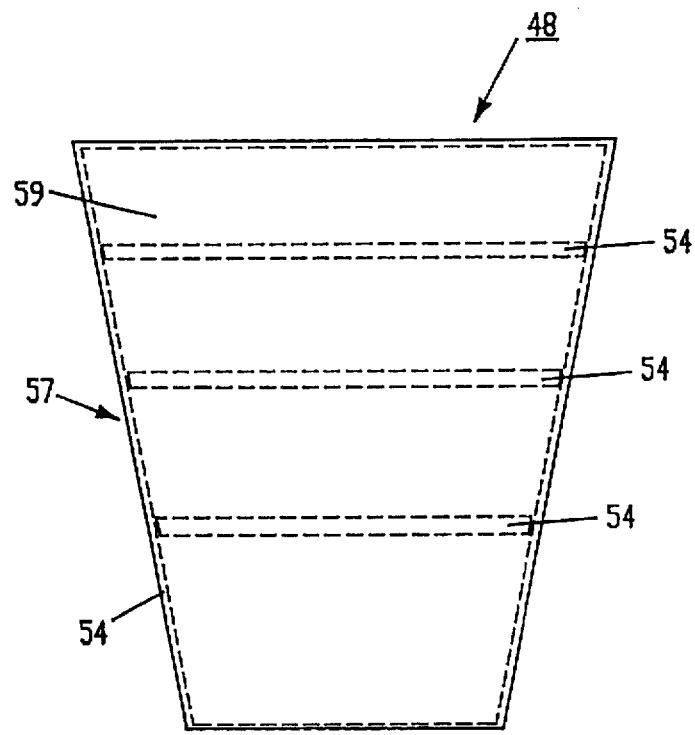
FIG. 16 is a bottom plan view of pneumatic bladder 48, bladder back panel 57.
Figure 17:
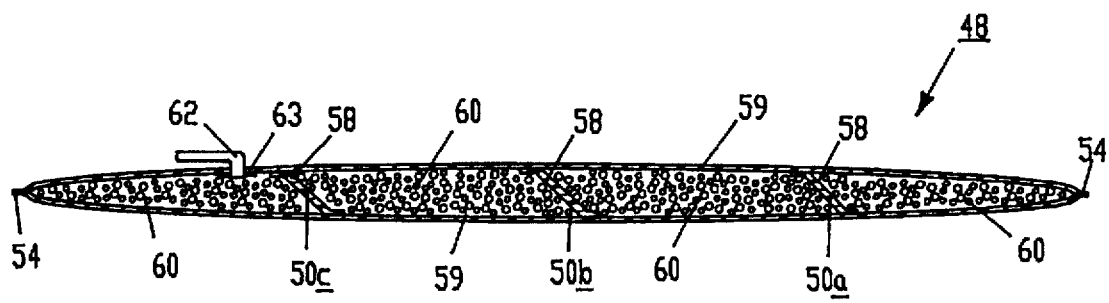
FIG. 17 is a simplified longitudinal section view through pneumatic bladder 48, illustrating off-set placement of expansion containment walls 50a–c.
Figure 18:
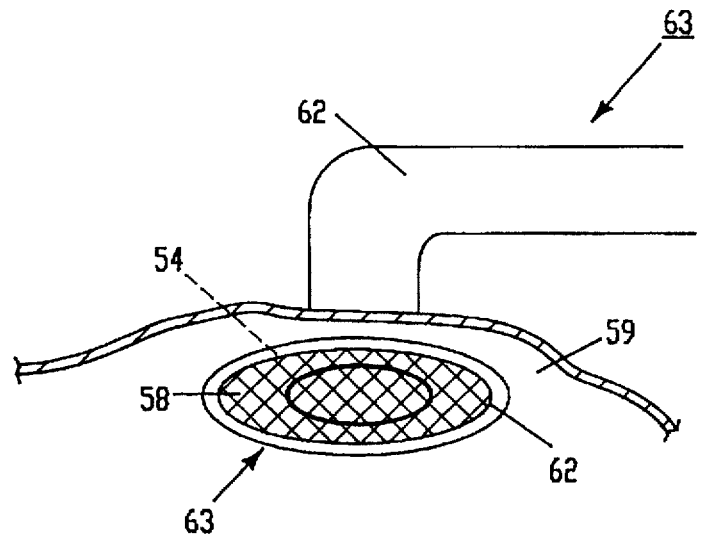
FIG. 18 is a simplified perspective view, partially broken away, of an angle connector 62 with angle connector filtration screen 63 attachment.

FIG. 15, showing bladder front panel 56, and FIG. 16, showing bladder back panel 57, located radio frequency heat seal 54 junctions of pneumatic bladder 48 bag construction and also seal 54 junctions of expansion containment walls 50a-c. Preferred embodiment of panel 56 and panel 57 is a vinyl coated nylon fabric that can be electronically heat sealed. FIG. 17 clearly shows walls 50a-c configuration with expanded foam beads 60 installed and panels 57 and 57 heat sealed 54. Preferred embodiment of walls 50a-c is vinyl coated nylon mesh fabric 58. Preferred embodiment of beads 60 is virgin polystyrene expanded foam beads mixed in dimension range from 1.5 to 3.0 millimeters. FIG. 18 shows detail of sealing 54 angle connector 62 and angle connector filtration screen 63 to panel 56. Preferred embodiment of screen 63 is vinyl coated nylon mesh fabric 68. Bladder 48 interior expansion containment walls 50a-c are a critical part of present invention as they assist in maintaining anatomical alignment during inflation-actuated fixation, and compartmentalize beads 60 minimizing displacement shift.

FIGS. 19 to 25: Attachment Views

Figure 19:
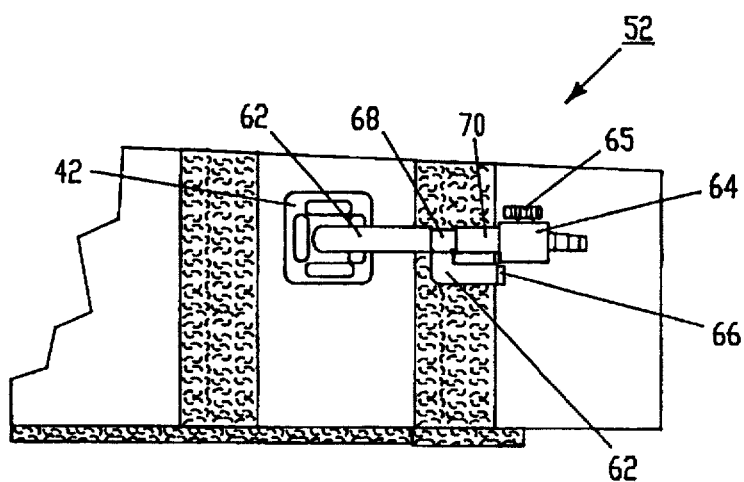
FIG. 19 is an exploded side elevation view of pneumatic control complex 52, as shown in FIG. 1.

FIG. 19 shows pneumatic control complex 52 connected to angle connector 62, after bladder 48 and framesheet 94 and enclosed in envelope 32, with connector 62 projecting through framesheet 94, outer sheet 36 of envelope 32, and tab 42. Complex 52 couples to connector 62 with connection of insert tee 68 hose barb. This connection is not bonded so that complex 52 may be easily removed from angle connector 62 for cleaning, repair or replacement of components. Converse end of insert tee 68 is bonded to tubing segment 70 which then is attached to control valve 64 dual hose barbs. Remaining perpendicular tee 68 is bonded to truncated angle connector 61 and pressure relief valve 66 is inserted into its apex. Control valve 64 preferred embodiment has dual hose barbs and in-line ball valve, regulated by a round valve handle 65 that prevents accidental opening during use. Because valve 64 hose barb is used to couple to tubing segment 70, it may be removed from complex 52 and directly connected to angle connector 62 if necessary. Pressure relief valve 66 preferred embodiment has medically predetermined automatic release capability at 40 millimeters of mercury. Relief valve 66 prevents over-inflation of pneumatic bladder 48 and provides a mechanism for assuring sufficient inflation pressure and checking straps 34a-f for excessive circumferential binding compression and closure tension.

FIGS. 20 and 21 show extremity hitch 72, of fabric structure, laid flat prior to application. Contact pad 76 is a rectangular cushioned pad with an affixed envelopment band 77. Kinetic tensing strap 78 is transversely connected to pad 76 so that upon application it encompasses injured extremity and reconnects to pad 76 through ladder locking buckle 88. Hitch 72 provides method and apparatus for an anatomically neutral, in-line point of attachment, that delivers continuous kinetic tension when traction is applied.

Preferred embodiments of contact pad 76 is of 10 millimeter even thickness micro-cellular high density close-call expanded polyethylene vinyl acetate foam 96, encased in urethane coated polyester fabric 80, known for its soft texture and durability. FIG. 20 shows hook tape 38a positioned and sewn into center of outer panel of pad 76 for adjustable closure of band 77. Single-fold nylon binding tape 84 is sewn on pad 76 long seam edges and transverse break lines are sewn at regular intervals across pad to accentuate padding and conformity, and increase comfort during utilization.

Preferred embodiments of envelopment band 77 consist of loop tape 44a sewn back to back with raw edges on long sides finished with binding tape 84, loose end finished with extruded hook tape 82 to enable attachment to band 77 in applied position.

Preferred embodiments of kinetic tensing strap 78 consist of elastic material 35 sewn onto pad 76 with web belting 92 sewn on tip to prevent material unraveling and easy removal from buckle 88 when threaded. Buckle 88 is attached by shortened length of elastic material 35, folded double and sewn on near opposing end of pad 76, as shown in FIG. 20.

Figure 22:
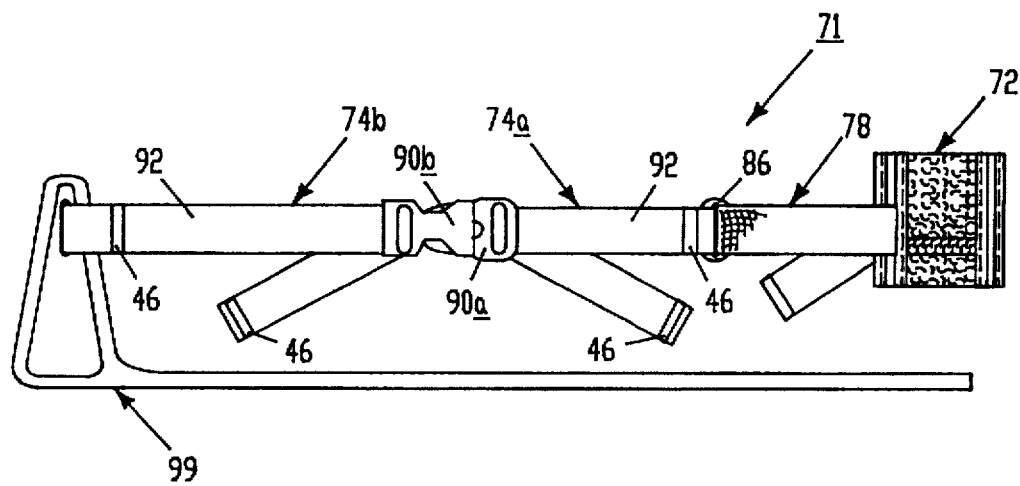
FIG. 22 is a side elevation view of detachable traction system 71, separated from integrated synergistic emergency splint 30, with traction tensing harness 74a–b and extremity hitch 72 attached in a position of function.

FIG. 22 displays entire detachable traction system 71 with extremity hitch 72 attached to traction tension harness 74a, traction tension harness 74b attached to traction bar 99, and harness 74a and 74b joined by quick coupling side release male buckle 90a and side release feral buckle 90b. Harness 74a is stored in connective position to hitch 72, and harness 74b is permanently affixed by weld 46 to bar 99, thus union of extremity hitch 72 to traction bar 99 is accomplished with only one quick attachment buckle 90a-b, and mechanical traction is easily accomplished by tensing loose ends of harness 74a or 74b in either direction, whichever is most convenient.

Figure 23:
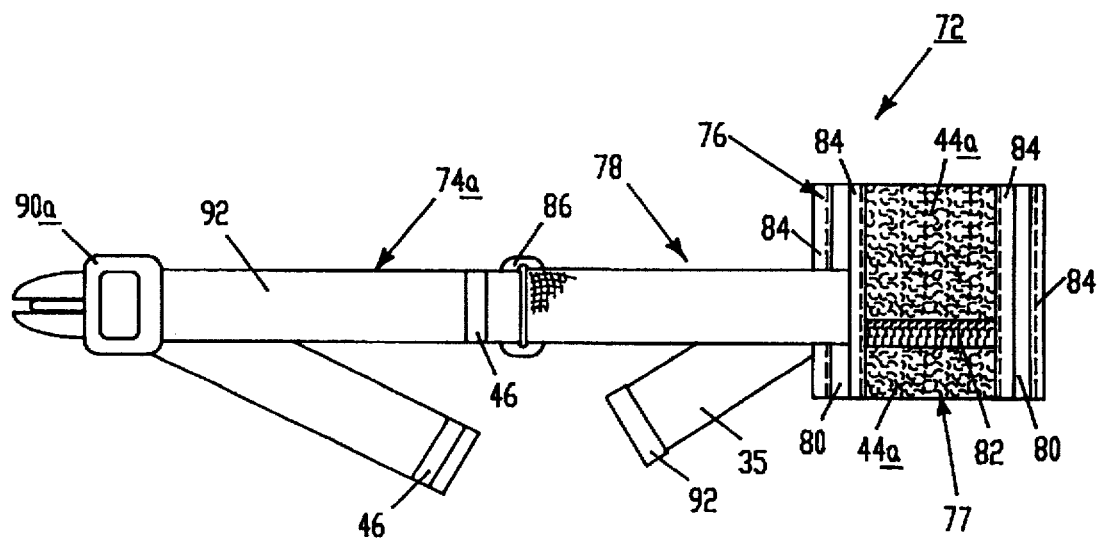
FIG. 23 is a detailed side view of extremity hitch 72 with traction tensing harness 74a, as shown in FIG. 22.

FIG. 23 details preferred embodiments of traction harness 74a and coupling devices. Harness 74a is comprised of web belting 92 attached to acetal simple connecting loop 86 by ultrasonic material weld 46 and threaded through buckle 90a tensional bars. Loose end apex of harness 74a is doubled back and secured to itself with weld 46 forming a tip which prevents accidental removal of buckle 90a. Connecting loop 86 is attached to hitch 72 by threading loop 86 on kinetic tensing strap 78, and then threading strap 78 through buckle 88 tensional bars, shown in FIG. 20 and 21.

Figure 24:
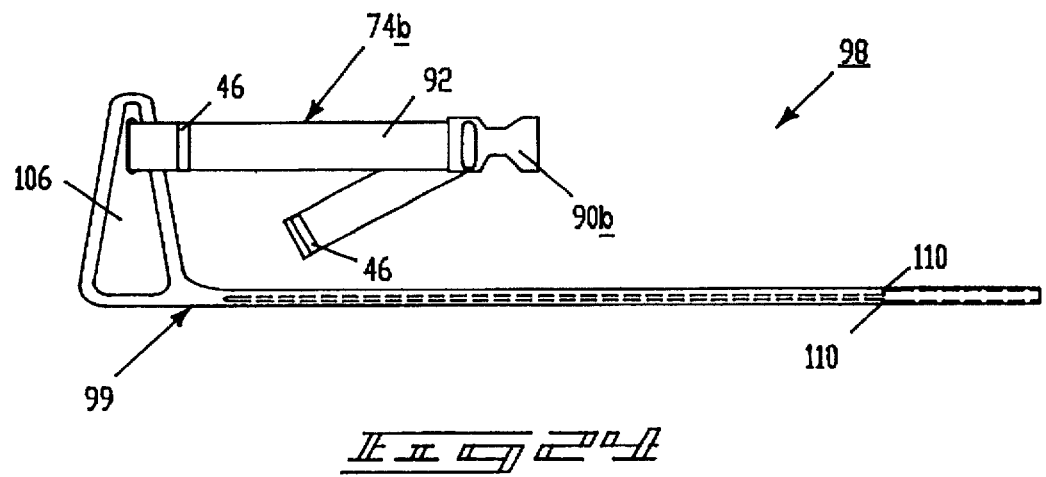
FIG. 24 is a detailed side elevation view of traction bar assembly 96, with traction tensing harness 74b, as shown in FIG. 22.

FIG. 24 details preferred embodiments of traction harness 74b and traction bar 99 attachment. Harness 74b is comprised of web belting 92 looping through slot in tip of bar 99 and affixed by material weld 46, then threaded through buckle 90b tensional bars. Loose end apex of harness 74b is doubled back and secured to itself with weld 46 forming a tip which prevents accidental removal of buckle 90b.

Figure 25:
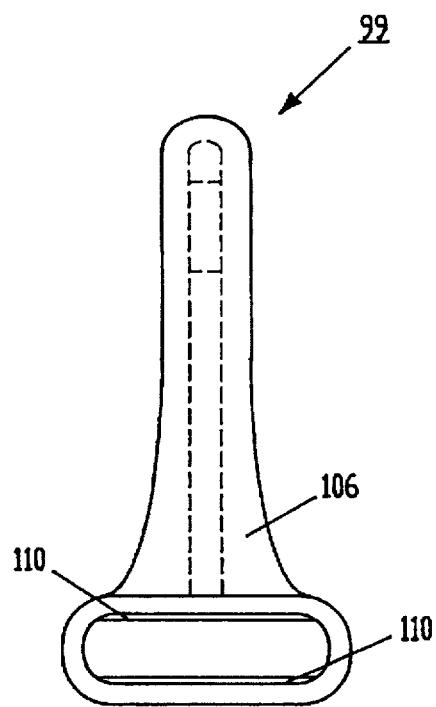
FIG. 25 is a detailed end view of traction bar 99, showing female coupling end that receives central stiffening monostay 100.

FIGS. 24 and 25 detail preferred embodiments of traction bar 99. Molded composite of high tensile strength, bar 99 is formed by resin transfer molding process which impregnates graphite fiber 106 with polyester matrix resins under heat and pressure, then vacuum is applied to closed-die mold forming part, it will be apparent to those skilled in the art that other molding and composite processes can be used to fabricate traction bar 99. Tip slot of bar 99 is diamond milled after resin transfer molding process.

FIG. 25 details an end view of traction bar 99 orifice showing monostay stop 110 as a simple thickening of internal wall structure recessed at a preferred distance of 50 millimeters from end of bar 99, with internal dimensions just large enough to permit coupling with end of monostay 100.

Operation of Invention

Operation of present invention will be clear when considered with foregoing description. The innovative integrated synergistic emergency splint 30 is of dependable anatomic multipurpose utilitarian design that incorporates five fundamental orthopedic methods of splint fixation in synergistic relationships, in one integrated emergency unibody splint apparatus, with layered components working together to provide unequaled safeguarding and comfort, improved immobilization, enhanced reliability, with mild, versatile, ergonomic apparatus utilization.

The first component layer is the heart of splint 30. It is an anatomically designed pliable unibody envelope 32 that has an external long axis medial monostay pocket 102 and a plurality of self-stowing, orbital compression isokinetic tensing straps 34a–f, which integrate synergistically with two other internally layered components for structural integrity. Envelope 32 utilizes a graphite fiber monostay 100 to provide rigid long axis stability, and is in itself a point of attachment for detachable traction system 71. Monostay 100 is removable when workable flexion is required in vacuum-actuated immobilization of an angulated extremity. Monostay 100 is housed in pocket 102 on envelope 32. Envelope 32 is wrapped around an injured extremity from its first open position, which is generally configured as a planar trapezoid with tapered sides, as shown in FIG. 4–6, and is then yieldingly malleable to a second closed position, and retained in place by envelope 32 straps 34a–f, as shown in FIG. 1–3. Envelope 32 straps 34a–f are manually expanded during application, providing orbital compression and becoming self-tensing through retraction, especially during bladder 48 vacuum contraction or conversely further expandable during inflation. Straps 34a–f expandable and retractable isokinetic format transfers its orbital point compression and closure tension energy from envelope 32 to internal stiffening framesheet 94, providing more uniform surface compression.

The second component layer comprises internal stiffening framesheet 94 which is critical for safeguarding and providing dependable soft immobilization, environmental protection, ease of application, and affords envelope 32 with its resilient contour shaping, and mechanism for energy transfer. Framesheet 94 must be resistant enough to safeguard from punctures and damage common to prehospital rescue environment, and supportive enough to provide envelope 32 with a structural long axis support base for supplemental immobilization. Framesheet 94 maximizes transfer and distribution of focused orbital pint compression and closure tensing energy from isokinetic tensing straps 34a–1 throughout framesheet 94, forming an enveloping long axis support base that constrains injured extremity. In addition, framesheet 94 provides an enveloping long axis support base upon which pilant pneumatic bladder 48 expanded polymer beads 60 may displace, and flow into apparatus contours and anatomical voids between injured extremity and bladder 48 surface. Supplementary safeguarding of bony prominent anatomic points are also afforded by framesheet 94.

The third component layer is comprised of a pliable pneumatic bladder 48 which contains multitudinous expanded polymer beads 60 that provide invaluable anatomical padding when splint 30 is providing synergistic combinations of rigid, soft, and traction-actuated fixation immobilization. When a vacuum is actuated within bladder 48, beads 60 draw together, compressing themselves without exerting circumferential pressure, into a rigid cast-like immobilizing structure on injured extremity. Pneumatic bladder 48 is divided into compartments by expansion containment walls 50a–c that communicate gases freely, which aid in maintaining anatomical alignment of an injured extremity when inflation pressure is actuated within bladder 48, by assisting in prevention of centralized spherical balloon type expansion from occurring within bladder 48. In addition, walls 50a–c compartmentalize beads 60 minimizing paramedical application displacement shifting when splint 30 is held or carried vertically to injured person.

Externally attached pneumatic control complex 52 safeguards injured person and supplies basic need for an open/closed pneumatic control valve 64 for maintaining vacuum or inflation pressures. The quantified pressure relief valve 66 prevents excessive over-inflation pressures from any cause, and is a mechanism for assuring adequate inflation pressures. Further, pressure relief valve 66 provides quick and easy quantified testing of splint 30 for excessive external compression pressure from isokinetic tensing traps 34a–f by simply applying inflation pressure into control valve 64. If relief valve 66 exhausts itself immediately, too much external compression pressure and closure tension has been applied to splint 30, and unibody envelope 32 straps 34a–f are in need of adjustment.

Detachable traction system 71 is comprised of a traction bar 99, a traction tensing harness 74a–b, and extremity hitch 72, as shown in FIG. 22. Detachable traction system 71 utilizes monostay 100 as a distal point of attachment for traction bar 99, and a proximal anchoring point at reinforced end of pocket 102 on envelope 32. When applied to a distal extremity, hitch 72 kinetic tensing strap 78 provides an anatomically neutral, in-line dynamic traction force when tensing. The padded anatomical long axis ribs on contact surface of hitch 72 provide for non-traumatic extremity utilization. Traction tensing harness 74a–b is tensed by pulling loose ends of harness 74a or 74b in either direction, whichever is most convenient, to point of providing incipient traction. A resulting countertraction force is applied to traction bar 99 and transferred to monostay 100 which yields slightly under compression, providing positive dynamic traction from anchoring point pocket 102 which dissipates residual energy within envelope 32, thereby eliminating specific anatomic pressure points. Splint 30 is not dependent on anatomy proximal to splinting apparatus to assure splint stabilization and actuation of traction through countertraction from proximal locus. With splint 30 this stability originates from overlaid skin surface area and underlying soft tissues exposed to uniform circumferential pressure that is applied to these anatomical structures by unibody envelope 32 through orbital compression isokinetic tensing straps 34a–f, stiffening framesheet 94, and pneumatic bladder 48, without pneumatics being employed, and rigidified by monostay 100 all of which synergistically produce an integrated rigid and soft fixation support base from which traction is founded. Further, if actuated, additional stability of vacuum fixation is available when minimal external circumferential pressure is desired or indicated, or conversely when external counter-pressure is desired, inflation fixation can be actuated. Integrated synergistic emergency splint 30 affords required amount of orthopedic traction and uniformly dissipates resulting countertraction forces within apparatus, transferring diversified energy to underlying anatomical structures in a manner that the injured person experiences no specific pressure points, apparatus adjustment or injured extremity movement.

SUMMARY, RAMIFICATION, CONCLUSION

An integrated synergistic emergency splint 30 of dependable anatomic multipurpose utilitarian design that incorporates live fundamental orthopedic methods of splint fixation in synergistic relationships to fortify extremity immobilization and provide automatic safeguarding in one emergency unibody splint apparatus. Present invention is comprised of integrated layered components operating synergistically to provide unequaled safeguarding and comfort, improved immobilization, enhanced reliability, with rapid, versatile, ergonomic apparatus utilization. The five known single purpose immobilization methods are listed as a paradigm to assist in summary of the new preferred method of multipurpose integrated synergistic immobilization provided by splint 30: 1. rigid fixation and soft fixation; 2. vacuum-actuated fixation and soft fixation; 3. vacuum-actuated fixation, rigid fixation, soft fixation; 4. inflation-actuated fixation, rigid fixation, soft fixation; 5. traction-actuated fixation, rigid fixation, soft fixation; 6. traction actuated fixation, vacuum-actuated fixation, rigid fixation, soft fixation; 7. traction-actuated fixation, inflation-actuated fixation, rigid fixation, soft fixation.

It is to be understood that foregoing description of accompanying drawings shall relate to preferred and illustrated embodiments of present invention. Various modifications may be employed without departing from sphere and scope of present invention. Thus, by way of example and not limitation, instead of envelope 32 forming a sealed bag, envelope sheet 36 could be placed over framesheet 94, bladder panel 56, and incorporated with bladder panel 57, forming a unibody structure with same components, using less fabric, but eliminating pneumatic bladder 48 replacement capability and adding to complexity of fabrication, repair, and paramedical cleaning and decontamination. The use of a flexible wide zipper for unibody envelope 32 sheet 36 and sheet 37 closure would have a different configuration than that illustrated. There can be many splint apparatus strap systems and many configurations of overlapping hook and loop covered portions on sheet 36 fabric of envelope 32 for holding splint 30 in place. In addition to monostay pocket 102, bilateral stiffening pockets could be incorporated onto envelope 32 for use with bilateral adjustable traction framework, and single shaft framework for application on medial or lateral aspects of injured extremity. Instead of detachable traction system 71 traction bar 99 having an internal monostay stop 110, bar 99 could slip over central stiffening monostay 100 making bar 99 adjustable with external stop configuration, conversely bar 99 could be inserted into monostay 100 with many different variations of stops and adjustments. Cannibalized components of splint 30, such as removable central stiffening monostay 100 with detachable traction system 71 could be employed on pneumatic counter-pressure shock garments, and many of the single purpose utility splints. The isokinetic action of extremity hitch 72 could be used on known static traction splints converting them to dynamic traction splints.

In addition, integrated synergistic emergency splint 30 function should not be limited to humans, but can be utilized on animals such as domestic large dogs, and for use with farm and range animals, such as horses, cows and so forth. Veterinary uses as well as medical uses of present invention are self-evident and are not to be limited in any way to suggested specific animal or human use. Accordingly, present invention is not limited to that precisely shown and described. Present invention may be made in various sizes and shapes depending upon body area to which it is applied. Present invention is unitary insofar as handling is concerned except for detachable traction system 71 which is placed in a smaller bag or pouch on outside of splint 30 storage bag or case.

It is understood that variations from form of present invention disclosed herein may be made without departure from spirit and scope of present invention, and that specification and drawings are to be considered as merely illustrative rather than limiting. Various features and advantages of present invention are thought to be clear from foregoing description. Various other features and advantages not specifically enumerated will undoubtedly occur to those versed in the art, as likewise will variations and modifications of preferred embodiment illustrated and described, all of which may be achieved without departing from spirit and scope of invention as defined by following claims. General design of individual parts of invention as explained above may be varied in accordance with requirements in regard to manufacture and production, while still remaining within spirit and principle of invention, without prejudicing novelty thereof.

I claim:

1. An integrated synergistic emergency splint for immobilizing a human extremity, said integrated synergistic emergency splint comprising:

a unibody envelope, said unibody envelope being a trapezoid shaped bag conforming to general anatomical shapes of human extremities;

said unibody envelope having a wide proximal base end and a distal top end;

said unibody envelope having an outer sheet, said outer sheet being non-abrasive, finely woven fabric with high tear strength and fluid immune;

said outer sheet having a plurality of self-stowing, orbital compression isokinetic tensing straps;

said outer sheet having a central monostay pocket for use with a removable central monostay;

said removable central monostay having a cushioning mold mask on an end thereof;

said outer sheet having a circular opening therethrough for accommodation of an angle connector;

said unibody envelope having an inner sheet, said inner sheet attaching to said outer sheet to form said unibody envelope;

said unibody envelope having a removable internal stiffening framesheet, said removable internal stiffening framesheet being disposed in the unibody envelope formed between said inner sheet and said outer sheet;

said unibody envelope having a pneumatic bladder, said pneumatic bladder being disposed in the unibody envelope formed between said inner sheet and said outer sheet;

said angle connector attaching to said pneumatic bladder;

a pneumatic control complex, said pneumatic control complex attaching to said angle connector and providing for inflation and evacuation of said pneumatic bladder;

said pneumatic bladder containing therein expanded foam beads and a plurality of permeable expansion containment walls; and, a detachable traction system, said detachable traction system being detachably attached to said central monostay of said unibody envelope.

2. The integrated synergistic emergency splint of claim 1, wherein said pneumatic control complex further comprises:

a manually operation control valve;

a pressure relief valve, said pressure relief valve being preset to open; and a connective fitting and tubing, said connective fitting and tubing being attached to said angle connector.

3. The integrated synergistic emergency splint of claim 2 wherein said detachable traction system further comprises:

a detachable traction bar, said detachable traction bar having a milled slot on an end thereof for reception of a portion of a traction tensing harness and a female socket on another end thereof for coupling with said central monostay;

said traction tensing harness having a nylon webbing, said nylon webbing being welded back onto itself through said milled slot of said detachable traction bar on an end thereof, and having a half of a side release buckle on another end thereof;

said traction harness having an extremity hitch, said extremity hitch being a contact pad having an envelopment band and a kinetic tensing strap; and, said kinetic tensing strap being attached to said contact pad on an end thereof and having a simple connecting loop and a half of a side release buckle on another end thereof, said half of a side release buckle complementing and attaching to said half of a side release buckle on said nylon webbing.

4. The integrated synergistic emergency splint of claim 3 wherein said plurality of self-stowing, orbital compression isokinetic tensing straps further comprise engageable hook and loop material sewn together with heavy elastic such that each of said self-stowing, orbital compression isokinetic tensing straps fold back against itself into a compact interlocked storage position.

* * * * *